US011249056B1

(12) United States Patent
Patel et al.

(10) Patent No.: US 11,249,056 B1
(45) Date of Patent: Feb. 15, 2022

(54) DIALYSIS BASED INVITRO DRUG RELEASE STUDY METHOD

(71) Applicants: Piyush Govindbhai Patel, Randolph, NJ (US); Jayrajsinh Sarvaiya, Gandhinagar (IN)

(72) Inventors: Piyush Govindbhai Patel, Randolph, NJ (US); Jayrajsinh Sarvaiya, Gandhinagar (IN)

(73) Assignee: OCIM PHARMACEUTICALS LLC, Randolph, NJ (US)

( * ) Notice: Subject to any disclaimer, the term of this patent is extended or adjusted under 35 U.S.C. 154(b) by 0 days.

(21) Appl. No.: 17/203,991

(22) Filed: Mar. 17, 2021

(51) Int. Cl.
*G01N 30/14* (2006.01)
*G01N 33/15* (2006.01)
*G01N 30/86* (2006.01)
*G01N 30/02* (2006.01)

(52) U.S. Cl.
CPC ......... *G01N 30/14* (2013.01); *G01N 30/8675* (2013.01); *G01N 33/15* (2013.01); *G01N 2030/027* (2013.01); *G01N 2030/146* (2013.01)

(58) Field of Classification Search
CPC .... G01N 30/14; G01N 30/8675; G01N 33/15; G01N 2030/027; G01N 2030/146
See application file for complete search history.

(56) References Cited

U.S. PATENT DOCUMENTS

2010/0221838 A1* 9/2010 Burgess ............... B01D 61/28
436/52

OTHER PUBLICATIONS

USP, "<711> Dissolution," United States Pharmacopeial Convention, General Chapter <711> Stage 6 Harmonization, Official Dec. 1, 2011. (Year: 2011).*
D'Souza, Susan, "A Review of In Vitro Drug Release Test Methods for Nano-Sized Dosage Forms," Advances in Pharmaceutics, Hindawi Publishing Corporation, vol. 2014, Aritcle ID: 304757, Publ. Nov. 20, 2014, DOI: https://doi.org/10.1155/2014/304757. (Year: 2014).*
Zuglianello, et al., "Assessing the In Vitro Drug Release from Lipid-Core Nanocapsules: a New Strategy Combining Dialysis Sac and a Continuous-Flow System," vol. 16, No. 6, Publ. May 19, 2015, DOI: 10.1208/s12249-015-0330-0. (Year: 2015).*

* cited by examiner

*Primary Examiner* — Jennifer Wecker
*Assistant Examiner* — Michael Paul Shimek

(57) ABSTRACT

The present invention relates to dialysis based in vitro drug release study method which mainly involves the use of a dialysis cartridge (A), a dissolution vessel (B), a receiver media vessel (C) and tubing's on the inlet and outlet ports (D, E, F, G) of the cartridge. When the pharmaceuticals complex dosage form is added to the dissolution vessel, diffusion of the soluble drug through the membrane of the dissolution cartridge assists in determining the release of drug from the complex dosage form. This study can be done by various methods as required by the complex dosage form. If the dosage form needs to go through dissolution followed by diffusion, the setup as described in Experiment 1 is arranged and the study is performed accordingly and if the dosage form needs to go through diffusion step only, the setup as described in Experiment 2 is arranged and the study is performed accordingly.

10 Claims, 4 Drawing Sheets

DIALYSIS BASED INVITRO DRUG RELEASE STUDY METHOD

TECHNICAL FIELD

The present invention relates to the application of dialysis cartridge in developing in vitro release test method for complex dosage forms used in the pharmaceutical industry.

BACKGROUND OF THE INVENTION

Dialysis is a treatment used to support a patient with insufficient renal function. In dialysis, excess water, solutes and toxins are removed from the blood using a machine. This treatment was invented in 1943 by a Dutch physician Willem Johan Kolff and is widely used throughout the world in patients with kidney problems. Currently dialysis with many variations is commonly used in the pharmaceutical industry for the separation of soluble drug molecules from insoluble molecules and complex fractions.

Various types of dialysis methods like tube dialysis, float-a-lyzer, side-by-side and other variations are used in the pharmaceutical industry to separate the soluble drug fractions in several complex dosage forms. In above mentioned methods, solubilized drug diffuses through the membrane into the receiver media filled in the membrane probe. This process can also be performed by reversing the drug formulation filled in the membrane and allow the drug to diffuse through its membrane into the receiver medium, this process is also called as retrodialysis. Receiver media used during the dialysis process could be prepared according to the drug solubility and membrane acceptability.

SUMMARY OF PRIOR ART

Microdialysis has been widely used in vitro test method in pharmaceutical industry for the separation of soluble drug from its dosage form, but due to certain physical limitation of the membrane property like lower surface area and thickness of the membrane, which controls the diffusion of soluble drug leads to delay in analyzing the drug release in real time from the dosage form dispersed in the donor system. To overcome this physical limitation of conventional dialysis, single hollow fiber dialysis was developed, which has higher surface area and lower membrane thickness, which allow the drug to diffuse faster than the normal dialysis tube or the membrane used in the separation of soluble drug from the dispersed one, due to this the single hollow fiber were initial used in in vitro testing of the biological tissue (CMA probe). The diffusion of the drug from the disperse system was measured in real time, as they do not have the longer path to cross due to lower membrane thickness and internal diameter. Hollow fiber dialysis can be setup either normal dialysis or retrodialysis, where samples are collected and analyzed using chromatographic system.

The internal volume of the single hollow fiber probe being 1 to 10 microliter based on the length of the probe, the amount of drug that diffuses from the retrodialysis setup into the surrounding medium, which is larger in volume (5 mL to 1000 mL) could lead to difficulty in analyzing the drug diffuse, due to chromatographic limitation of estimating the analyte due to higher dilution by the receiver media. This issue would not have a raised with the normal dialysis setup, as donor side has extremely high concentration, which need to diffuse into lower receiver media. Normal dialysis would not have issue with freely soluble drug as it will be below its supersaturation level, but for poorly soluble drug, dialysate having lower volume and less time to diffuse it will show slower release from the media. To overcome the limitation of single probe retrodialysis, a new experimental dialysis setup using a dialysis cartridge which contain multiple single hollow fiber probe, with a higher fill volume capacity was developed to overcome the limitation of the chromatographic system. Dialysis cartridge have been used in many applications like blood purification, protein purification, concentrating a solution and many biotechnology purposes, they have also use dialysis cartridge, mimicking the function of kidney to predict the drug removal process, but have never been used for testing in vitro release of drug from solution or dispersed system, which need to undergo dissolution and diffusion process, as it required mathematical modelling to understand the property a membrane. This experimental setup will help to resolve most of the technical issue faced by the single hollow fiber probe, dilution, which will be further discussed in the experiment section.

SUMMARY OF THE INVENTION

The present invention relates to dialysis based in vitro drug release study method in which rapid in vitro diffusion of a soluble drug from the complex dosage forms such as suspensions, emulsions, liposomes, and other pharmaceuticals dosage can be evaluated. The present invention provides the information for the physical setup and the data analysis of the rapid in vitro dialysis method. Various experiments have been designed to provide the setup insight for the application of dialysis cartridge in determining drug release. In one embodiment of the invention both dissolution and receiver media are in continuous flow which is useful when the dosage form needs to go through dissolution followed by diffusion. In another embodiment of the invention, as the drug has to go through diffusion step only, the dosage form is stored in the cartridge and the receiver media keeps circulating which collects the soluble diffusible drug from the complex dosage form. Other aspects, features and advantages of the invention will be apparent from the description, drawings and from the claims.

DETAILED DESCRIPTION

In biochemistry, dialysis is the process of separating molecules in a solution by the difference in their rates of diffusion through a semi-permeable membrane such as dialysis tubing. It is a spontaneous separation process of suspended colloidal particles from dissolved ions or molecules of small dimensions through a semi-permeable membrane. The semi-permeable membranes are commonly made of cellulose, modified cellulose or synthetic polymer (cellulose acetate or nitrocellulose). Due to the pore size of the membrane, larger molecules in the solution cannot pass through the membrane, thereby restricting their diffusion from the sample chamber. However, smaller molecules freely diffuse across the membrane and obtain equilibrium across the entire solution volume.

Dialysis cartridges have been widely used in the field of gene therapy, perfusion cell culture, dynamic dialysis, and hemodialysis. However, it has not ever been used to determine the in vitro drug release from complex pharmaceutical dosage forms.

The present invention relates to dialysis based in vitro drug release study method from complex dosage forms which uses a dialysis cartridge for determining the drug release from complex dosage forms. The present invention can be setup as discussed in the following experiments according to the requirement of the dosage form.

Experiment 1

Figure 1:
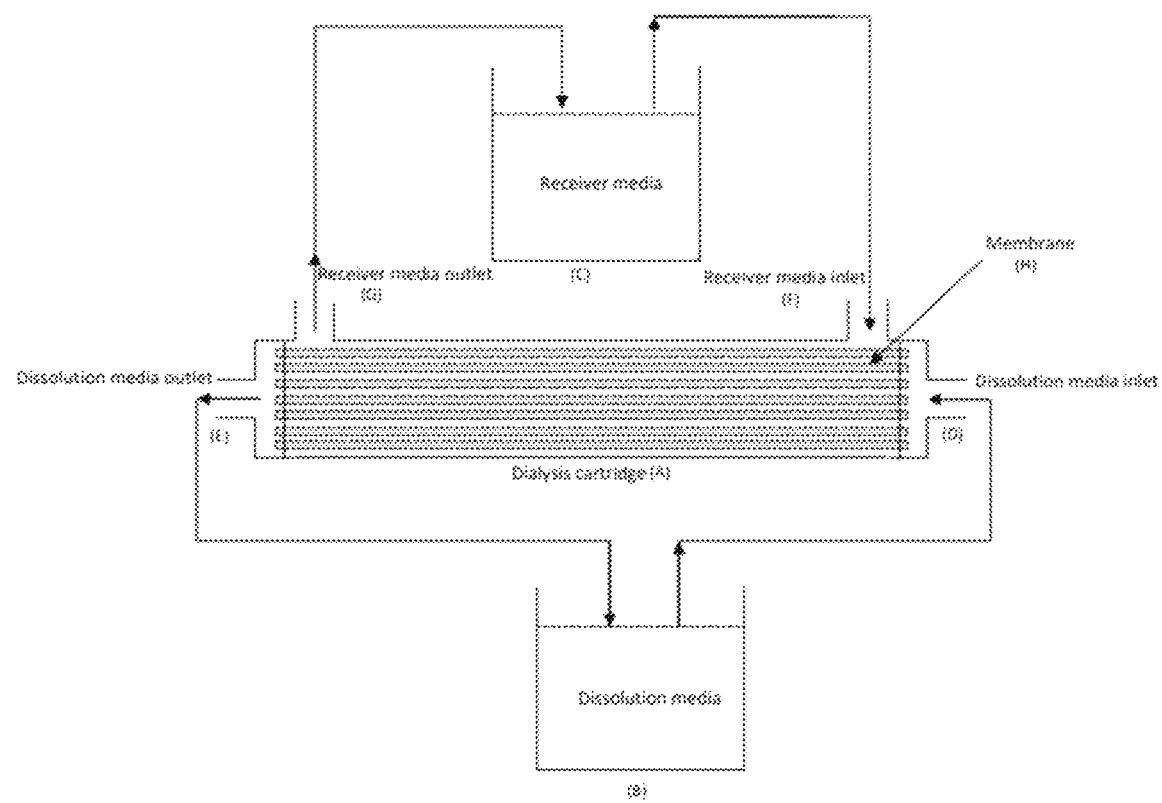
FIG. 1 gives the diagram of the setup used to determine in vitro drug release when the dosage form needs to go through dissolution followed by diffusion.

When any complex dosage form requires dissolution followed by diffusion for determining the in vitro drug release, the experiment setup as shown in FIG. 1 in the first experiment setup, dialysis cartridge (A) can be held parallel or vertical or in slightly inclined position or horizontal position. Once the cartridge is properly positioned, open all the inlet and outlet ports (D, E, F and G) of the cartridge. Connect all the inlets and outlets of the cartridge with the tubing firmly. The tubing's from the inlet (D) and from the outlet (E) are connected to dissolution vessel (B) while the tubing's from the inlet (F) and from the outlet (G) are connected to the receiver media vessel (C) as shown in the FIG. 1. Dissolution vessel and receiver vessel can be water jacketed beakers or vessels surrounded by temperature controlling pad to control the temperature of the media. The inlet tubing to the cartridge from both dissolution vessel (B) and receiver media vessel (C) pass from their respective vessels through the pump, which control the flow of media from the vessels to the cartridge.

Initially the dissolution vessel and receiver vessel are filled with the required dissolution media, which is similar in composition so that the drug can diffuse through the concentration gradient. Once the cartridge is filled with the media within and outside the membrane, the volume of the media is maintained in both the vessels. Then the desired quantity of dosage form containing the drug is added in the dissolution vessel (B), which is maintained with constant stirring. Tubing carrying the dissolution media through the pump into the cartridge at the inlet port (D) will pass through the membrane packed in the cartridge and will pass back to the vessel from the outlet port (E). During this passage the soluble drug diffuses into the receiver media which is carried back to the receiver media vessel from the outlet port (G).

Apart from the setup described above, this experiment can also be done in the following manner. Fresh receiver media enters the dialysis cartridge at a very slow flow rate and exits through the outlet in a different vessel. Due to this, a constant sink condition is maintained and the possibility of reaching the equilibrium concentration in the cartridge is avoided. In such a setup 100% drug release can be determined from the dissolution media. Once the dissolution process begins, the sample can be collected from the receiver media at regular intervals to determine the amount of drug released.

Figure 3:
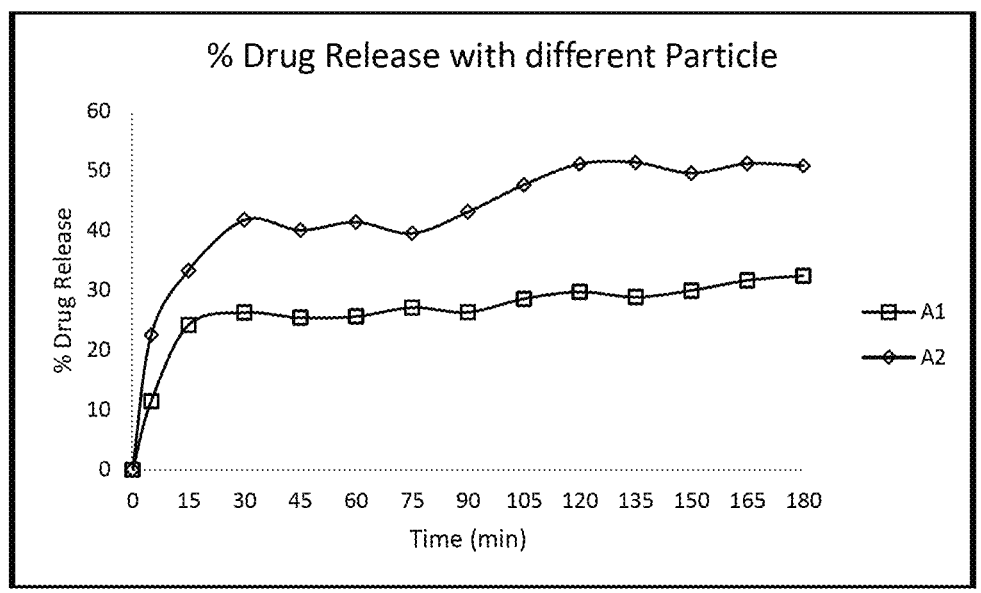
FIG. 3 gives the dissolution profile of drug release with different particle size using dialysis setup as Experiment 1.

To determine the release of dexamethasone from a complex suspension, formulation with different particle size was prepared and studied for drug release through this method using water with 0.1% Sodium Lauryl Sulfate (SLS). But before performing the drug release, each dialysis cartridge needs to be calibrated for its membrane property, which can affect the diffusion of soluble drug. To characterize the membrane of dialysis cartridge, a fraction recovery experiment was carried out with the similar setup which will be used for determining the drug release from the dispersed system, the only difference was use of 1% SLS in water to maintain the sink condition for the drug, as fraction recovery experiment needs to be performed on solubilized drug. This fraction recovery experiment will take membrane properties into consideration, while calculating the release of drug. The variation in particle size was recognized through difference in drug release profile as seen in FIG. 3.

Experiment 2

Figure 2:
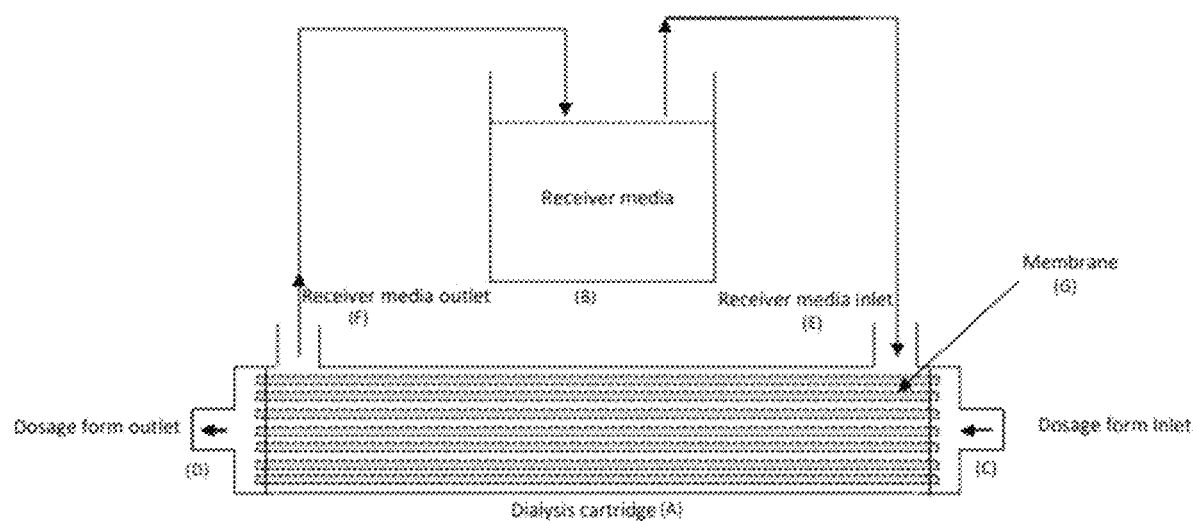
FIG. 2 gives the diagram of the setup used to determine in vitro drug release when the dosage form needs to go through diffusion only.

If in a complex dosage form, only the step of diffusion is required to determine the in vitro drug release, the experiment is set up as shown in FIG. 2. in the second experiment setup, the dialysis cartridge is filled with the dosage form where the drug is present in the soluble or complex form. This dosage form is passed through inlet (C). Once the cartridge is filled, both inlet (C) and outlet (D) are locked. Then the receiver media is set into circulation through the cartridge, from outside the membrane wall, which carries the available free soluble drug, back from the outlet (F) into the receiver media vessel (B). In this manner the soluble diffusible drug is collected from the complex dosage form.

Figure 4:
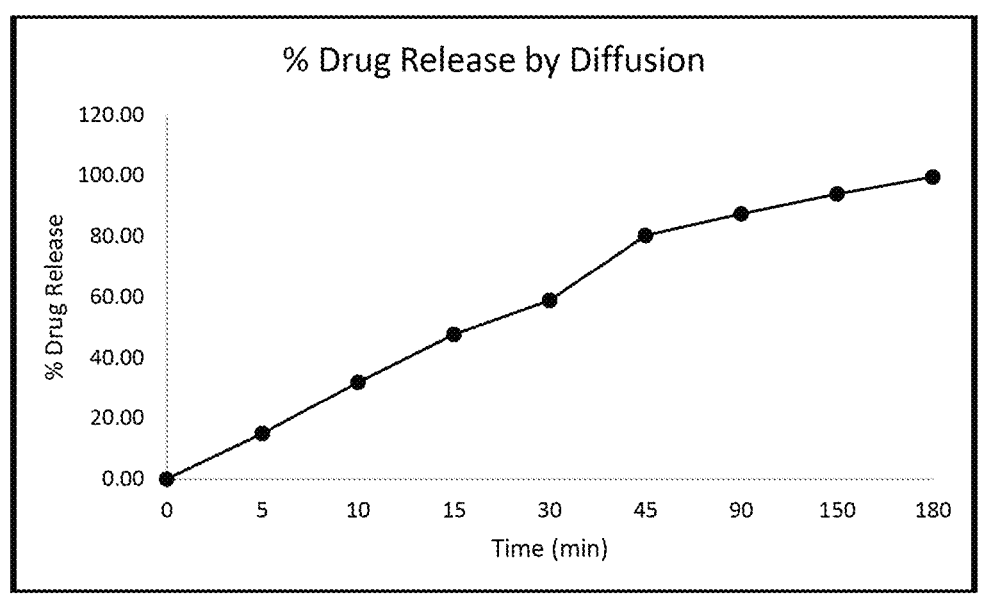
FIG. 4 gives the dissolution profile of drug release with different particle size using dialysis setup as Experiment 2.

Apart from the setup described above, this experiment can also be conducted in the following manner. According to the second setup, fresh receiver media enters the dialysis cartridge at a very slow flow rate and exits through the outlet in a different vessel. Due to this a constant sinking condition is maintained and the possibility of reaching the equilibrium concentration in the cartridge is avoided. Hence 100% drug release determination can be done from the diffusible dosage form. In this setup too, once the dissolution/diffusion process begins, sample can be collected from the receiver media at regular intervals to determine the amount of the drug released. FIG. 4 shows 100% drug release from dexamethasone emulsion product within 180 minutes when dialysis cartridge with surface area of 1.05 $m^2$ and effective length of 200 mm is used. The flow rate in receiver and donor compartment circulation inlet and outlet piping was kept 50 mL per minute. Sampling was done at predefined time interval with buffer replenishment with the fresh buffer in the receiver compartment followed by High Performance Liquid Chromatography (HPLC) based quantitative analysis of the drug.

The polymeric cartridges-based dialysis system and its method of use has the discriminatory ability for in vitro release testing of liposomes and other dispersed formulations. The method was able to discriminate between suspension formulations of different particle, which can also used to discriminate the formulation having different physicochemical properties. Discrimination can also be achieved for the extruded and non-extruded formulation variants of the same lipid in liposome product. This dialysis method is a reproducible and discriminatory method which can help in product development; quality assurance; and regulatory process of disperse dosage forms.

A few experiments of the present invention have been described. Nevertheless, it will be understood that various modifications may be made without departing from the spirit and scope of the invention. Accordingly, other implementations are within the scope of the following claims.

We claim:

1. Dialysis based in vitro drug release study method for determining drug release from complex dosage forms, comprising: a dialysis cartridge (A) comprising hollow fiber dialysis probes, an inlet port D configured to carry a dissolution media into the dialysis cartridge (A), an inlet port F configured to carry a receiver media into the dialysis cartridge (A), an outlet port E configured to carry the dissolution media out of the dialysis cartridge (A), an outlet port G configured to carry the receiver media out of the dialysis cartridge (A), a dissolution vessel (B) containing a required dissolution media; a receiver vessel (C) containing the same media as used in the dissolution vessel, and tubing configured to allow fluidic communication from inlet D and outlet E to the dissolution vessel (B), said tubing further configured to allow fluid communication between inlet F and outlet G to the receiver vessel (C); and wherein both the dissolution media and receiver media are in continuous flow throughout the dialysis cartridge.

2. The dialysis based in vitro drug release study method of claim 1, wherein the dialysis cartridge is made up of Polysulfone, surface modified polysulfone, cellulose acetate, chitosan, poly (ether sulfone), polyacrylonitrile, ethylene-vinyl alcohol copolymer, poly (methyl methacrylate) or poly (vinyl alcohol), either alone or in combination.

3. The dialysis based in vitro drug release study method of claim 1, wherein a length of dialysis cartridge is from 11 cm to 70 cm and effective surface area for a dialysis is from 20 $cm^2$ to 2 $m^2$.

4. The dialysis based in vitro drug release study method of claim 1, wherein a molecular weight cutoff (MWCO) of a dialysis membrane is from 15 kilodalton (kD) to 750 kD.

5. The dialysis based in vitro drug release study method of claim 1, wherein an inlet tubing to a cartridge from both the dissolution vessel (B) and receiver vessel (C) pass from their respective vessels through a pump, which controls the flow of media from the vessels to the cartridge.

6. The dialysis based in vitro drug release study method of claim 1, wherein a first experiment setup involves holding the dialysis cartridge (A) in parallel, vertical or slightly inclined position such that a cartridge (A) be filled using a cartridge holder.

7. The dialysis based in vitro drug release study method of claim 1, wherein a first experiment, displayed in FIG. 1, involves the following steps: Initially filling a cartridge (A) with a media within and outside a membrane and a volume of media is maintained in both the vessels;

adding a desired quantity of dosage form containing the drug to the dissolution vessel (B), which is maintained with constant stirring;

carrying the dissolution media through the pump into the cartridge at inlet port (D) through tubing;

passing the dissolution media through the membrane packed in the cartridge and passing the dissolution media back to the vessel from the outlet port (E); and while passing, having the soluble drug diffuse into the receiver media which is carried back to the receiver media vessel from the outlet port (G).

8. The dialysis based in vitro drug release study method of claim 5, wherein a first experiment, displayed in FIG. 1, involves the following steps: flowing fresh receiver media through the dialysis cartridge, such that the fresh receiver media exits through an outlet port (G) into a different vessel such that a constant sink condition is maintained and the possibility of reaching an equilibrium concentration in the cartridge (A) is avoided; and, wherein, after a dissolution process begins, the sample is collected from the receiver media at regular intervals to determine an amount of drug released.

9. The dialysis based in vitro drug release study method of claim 1, wherein a second experiment, displayed in FIG. 2, involves the following steps: filling the dialysis cartridge with a dosage form of the drug, wherein the drug is present in a soluble or complex form and for which the dosage form passes through an inlet port (C);

wherein after cartridge (A) is filled, both inlet port (C) and outlet port (D) are locked; and wherein a receiver media is then circulated through the cartridge from outside a membrane wall, which carries an available free soluble drug, back from the outlet (F) into the receiver vessel (B) to collect a soluble diffusible drug from a complex dosage form.

10. The dialysis based in vitro drug release study method of claim 1, wherein alternatively the a second experiment involves the following steps: flowing fresh receiver media through the dialysis cartridge, such that the fresh receiver media exits through an outlet port (F) into a different vessel such that a constant sink condition is maintained and the possibility of reaching an equilibrium concentration in the cartridge (A) is avoided; and, wherein, after a dissolution process begins, the sample is collected from the receiver media at regular intervals to determine an amount of drug released.

* * * * *